United States Patent [19]

Cawood

[11] Patent Number: 4,458,705
[45] Date of Patent: Jul. 10, 1984

[54] TRAY AND BASIN COMBINATION

[76] Inventor: Charles D. Cawood, 11527 N. Lou Al Ct., Houston, Tex. 77024

[21] Appl. No.: 453,137

[22] Filed: Dec. 27, 1982

[51] Int. Cl.³ .............................................. B08B 3/04
[52] U.S. Cl. .................................... 134/135; 134/137; 206/369; 422/300
[58] Field of Search .................... 134/135, 137, 84, 85; 312/306, 320; 220/230; 422/300; 206/363, 369, 370, 818; 335/295, 207

[56] References Cited

U.S. PATENT DOCUMENTS

| | | | |
|---|---|---|---|
| 2,521,723 | 9/1950 | Hubbell | 335/207 |
| 2,978,110 | 4/1961 | Haskins | 206/369 |
| 3,419,346 | 12/1968 | Nicholas | 422/300 |
| 3,478,758 | 11/1969 | Davies | 134/135 |
| 4,053,280 | 10/1977 | Salisbury | 134/135 |

FOREIGN PATENT DOCUMENTS 1216548 11/1959 France .............................. 206/818

Primary Examiner—Stephen Marcus
Assistant Examiner—Renee S. Kidorf
Attorney, Agent, or Firm—Tilton, Fallon, Lungmus

[57] ABSTRACT

A tray and basin combination particularly useful for soaking medical implements, such as urological instruments, in a treatment solution. In use, the tray is self-elevating within the basin; however, a magnetic retainer is provided for selectively holding the tray in a lowered condition, with the articles supported thereby immersed in the treatment solution, until the treatment is completed and the tray is to be raised.

15 Claims, 4 Drawing Figures

TRAY AND BASIN COMBINATION

BACKGROUND AND SUMMARY

Urological instruments are commonly disinfected by soaking them prior to use in a solution of buffered glutaraldehyde or some other strong disinfecting or sterilizing solution. While such a "cold soaking sterilization" procedure is most frequently associated with urological instruments, it may be used for disinfecting any implements which are not capable of withstanding autoclaving temperatures or cannot conveniently be sterilized by other means. Similar procedures are used for sterilizing or disinfecting dental instruments, hair cutting and styling implements, and the like.

Quite typically, all of the instruments required for a selected medical procedure are placed in a stainless basin containing the disinfecting or sterilizing solution and are simply soaked in the solution for a period of approximately 10 to 20 minutes. Thereafter, the instruments are grasped and lifted from the basin, rinsed, and laid out on a sterile-draped surface in the area of patient examination or operation.

To facilitate removal of the instruments from a soak solution, it has also been a practice to place the instruments in a basket or tray which may in turn be lowered into and lifted from the solution. In such a case, it is important that the entire tray be immersed along with the instruments; otherwise, a portion of the tray (such as a handle) would remain untreated and subsequent contact with that portion might contaminate the treated instruments. The result is that various systems have been devised, notably elaborate and complex, for achieving total tray immersion and increasing the accessibility of the instruments following treatment. For example, in U.S. Pat. No. 2,231,790, rocking arms, toothed wheels, and lugs are provided for shifting the tray between its immersed and extracted positions. U.S. Pat. No. 3,419,346 discloses spring means for elevating a tray and solenoid latching means for holding it in lowered position, but neither total immersion of the tray nor removability of the tray from the basin are possible. In U.S. Pat. No. 2,556,495 the tray is operatively linked to a hinged cover for the basin, but again, total immersion of the tray, or ease of separability of the tray from the basin (so that the tray may be used as a carrier for transporting instruments from the sterilizing station to the place where the instruments are to be used) are not disclosed. Other U.S. Pat. Nos. illustrative of the state of the art are 1,862,963, 1,187,498, 3,478,758, and 4,196,166.

One aspect of this invention therefore lies in providing a tray and basin combination which is uncomplicated in structure and operation and which at the same time insures complete immersion of the tray and its contents, permits complete removal of the tray from the basin for transporting the treated implements, and is easily operated to shift the tray and its contents from a lowered and fully-immersed position to a raised and readily accessible position without requiring the user to reach into the treatment solution within the basin or to grasp the tray to shift it between its lowered and raised positions.

Briefly, the apparatus includes an open-topped plastic basin having side and bottom walls defining a well for holding a treatment solution, and a tray adapted to be received within the well for supporting articles to be treated. The side walls of the basin have a height substantially greater than the tray to accommodate vertical movement of the tray between raised and lowered positions in the treatment solution. Lifting means are provided for urging the tray into its raised position; in the disclosed embodiment, such lifting means takes the form of air chambers or compartments formed in the tray to provide a buoyancy sufficient to lift the tray and its contents in the fluid medium. For selectively retaining the tray and its contents in lowered position, magnetic anchoring means are provided for overcoming the upward force exerted by the lifting means. The magnetic anchoring means includes a horizontal slide member supported by the bottom wall of the basin and capable of being shifted horizontally between first and second positions of adjustment. The slide member and the underside of the tray are provided with magnetic elements and, when the slide member is in its first position and the tray is lowered, the magnetic elements of the respective parts are aligned in close proximity and function to retain the tray in its lowered position. When the slide member is shifted into its second position, the magnetic elements are shifted out of their positions of attraction, allowing the tray to move upwardly into its raised position. The magnetic elements of at least one of the members (i.e., the slide member or tray) take the form of permanent magnets; where the magnetic elements of both members constitute permanent magnets, such magnets may be arranged to provide a repelling force when the slide member is shifted into its second or extended position, such repelling force supplementing the upward force of the lifting means to promote release and upward travel of the tray and its contents when the treatment process is completed.

Other features, advantages, and objects of the invention will become apparent from the specification and drawings.

DRAWINGS

DESCRIPTION OF PREFERRED EMBODIMENTS

Figure 1:
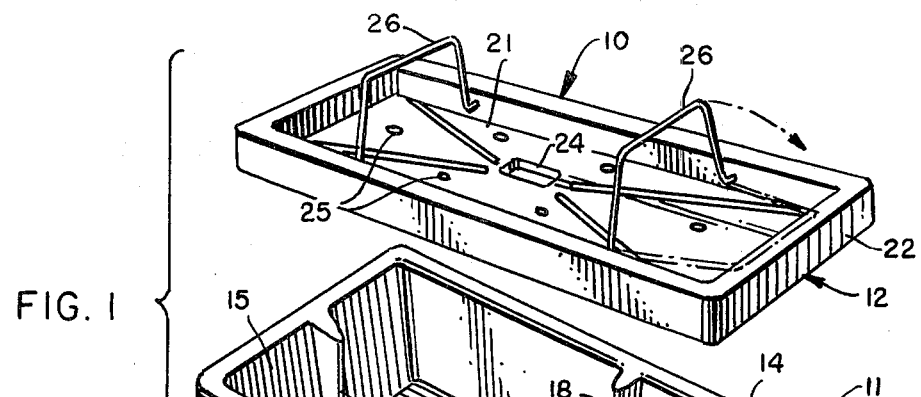
FIG. 1 is a perspective view of the apparatus showing the tray and basin in separated condition.
Figure 2:
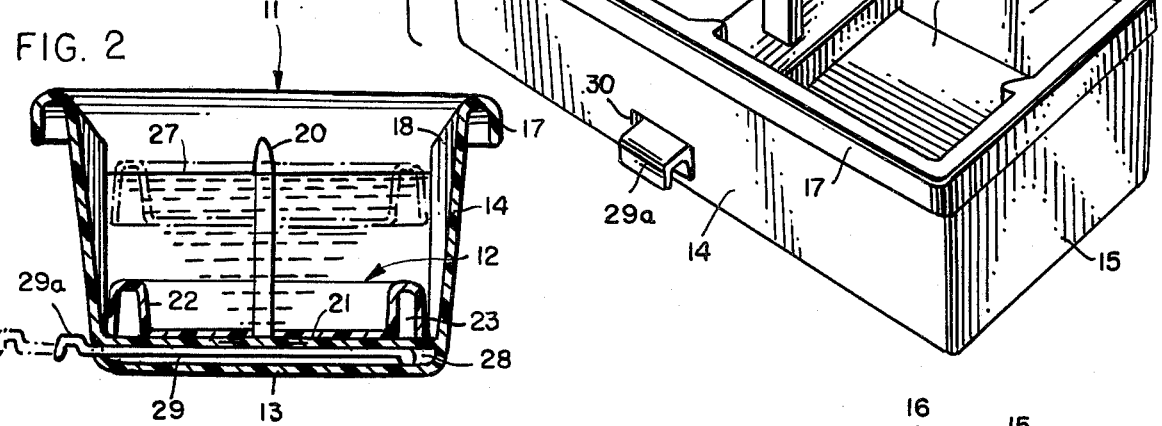
FIG. 2 is a vertical transverse sectional view of the basin with the tray in its lowered position therein, the tray also being depicted in broken lines in its raised position.
Figure 3:
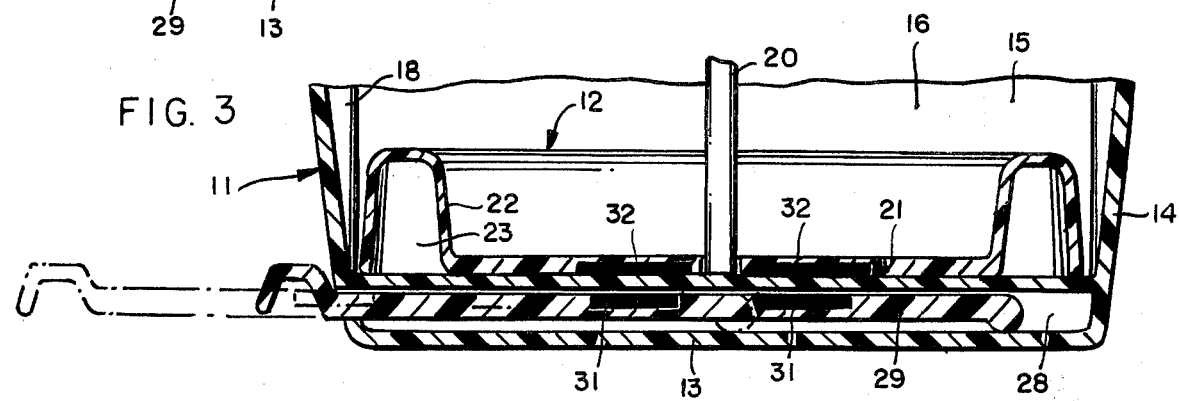
FIG. 3 is an enlarged fragmentary sectional view showing details of the construction of FIG. 2.

Referring to FIGS. 1–3, the numeral 10 generally designates an apparatus comprising a basin 11 and a tray 12. Both components are preferably formed of a tough, relatively rigid, plastic material such as polypropylene or high-impact polystyrene. Whatever the material selected, that material should be durable, non-galvanic when exposed to a typical treatment solution and the metal instruments or other articles to be carried by the tray, and non-magnetic (i.e., not magnetically attractable). A suitable cover formed of similar material may also be provided; a cover is not shown because it would be entirely conventional and form no part of this invention.

The basin 11 includes a bottom wall 13, and upstanding side walls 14 and 15 formed integrally therewith. In the form shown in FIG. 1, the basin is elongated and generally rectangular in outline with walls 15 serving as end walls. The basin is open-topped, defining a well or chamber 16 for supporting a glutaraldehyde solution or other treatment solution. Along its upper perimeter, the basin is provided with a continuous outwardly and downwardly turned flange or rim 17. Vertical guide ribs 18 protrude inwardly from the side walls 14 and 15 and provide vertical edges for guiding movement of tray 12 within the well of the basin. A central post or column 20 extends upwardly from bottom wall 13 and also assists in guiding vertical movement of the tray.

The horizontal tray 12 is also rectangular in outline and is dimensioned to move easily, without interference from the side walls of the basin, between the lowered position shown in solid lines in FIG. 2 and the raised position depicted in broken lines in the same illustration. As shown most clearly in FIGS. 1 and 3, the shallow tray has a horizontal bottom wall or panel 21 bordered by a perimetric rim 22 of inverted U-shaped cross sectional configuration. The rim defines a perimetric air chamber 23 for giving buoyancy to the tray when the apparatus is in use. In the embodiment illustrated, the chamber 23 is in the form of a downwardly-facing channel which is open along its lower limits; however, it is to be understood that if desired the bottom of the channel may be closed so that the perimetric air chamber is entirely sealed.

A central aperture 24 is provided in bottom panel 21 for slidably receiving the basin upstanding post 20. Other apertures or perforations 25 may be provided in panel 21 to prevent the liquid contents of the basin from interfering with movement of the tray between its raised and lowered positions. The tray may be equipped with one or more folding handles 26, two such handles being shown in FIG. 1. Such handles, when not in use, swing downwardly into the lowered positions indicated in the drawing so that they may be fully exposed to the treatment solution within the basin.

The depth of the tray (i.e., the height of rim 22) may be varied considerably depending on the instruments or other objects to be supported by the tray. Ordinarily, a shallow tray of the type shown is believed to be most suitable and, in any event, the vertical dimension of the tray is substantially less than the depth of well 16. Complete immersion of the tray and its contents in the treatment solution 27 in basin 11 is therefore readily achieved. In general, the level of the solution 27 should approximate the level shown in FIG. 2. The buoyancy of the tray with its air chamber 23 should be sufficient to cause the tray and its contents (not shown) to assume an elevation at least as high as the position represented in broken lines in FIG. 2.

A transversely-extending compartment 28 is formed in the basin's bottom wall 13, the compartment being located equidistant from end walls 15. A slide member 29, equipped with a handle 29a, is slidably received within compartment 28 through access opening 30. The elongated slide member may be shifted between an inwardly retracted first position, represented in solid lines in FIGS. 2 and 3, and an outwardly extended second position shown in broken lines.

Referring to FIG. 3, it will be seen that magnetic elements 31 and 32 are provided by the slide member 29 and tray 12, respectively. In the illustration given, the slide member is provided with two such elements 31 in the form of permanent magnets embedded (either fully or partially) in the plastic material of the slide member. The elements 31 are located equal distances from the longitudinal vertical midline of the basin, when the slide member 29 is fully inserted within its compartment, to equalize the downward magnetic force exerted upon the tray 12. Similarly, the tray may be provided with a pair of magnetic elements 32 also centrally located with respect to the tray's bottom panel 21. Elements 32 may take the form of permanent magnets arranged to be positioned directly above magnetic elements 31 when slide member 29 is fully inserted and the tray is in its lowered position (FIG. 3); in such a case, elements 32 must be oriented so that the faces thereof in direct opposition to those of magnetic elements 31 are of opposite polarity. However, elements 32 need not be permanent magnets and, in the embodiment of FIGS. 1-3, simply take the form of plates of ferromagnetic or paramagnetic material capable of being magnetically attracted by permanent magnets 31 with a force sufficient to overcome the buoyancy of the tray 12 in treatment solution 27. The plates may be formed of steel and be partially or totally embedded within the bottom panel 21 of the tray.

When the slide member is shifted outwardly into its tray-releasing position, the magnetic elements 31 and 32 of the slide member and tray are no longer in vertical alignment, and the tray is therefore released for upward movement by buoyant action of air chambers 23. With the tray in its raised position, a user may easily grasp the tray (using handles 26 if provided) and remove the tray and its contents from the treatment solution. Conversely, when a load of instruments or other articles are to be treated, a user simply lowers the tray into the treatment solution while the slide member is in its fully-inserted position. The handles 26, when released, are free to swing downwardly into the treatment solution surrounding the lowered tray.

Figure 4:
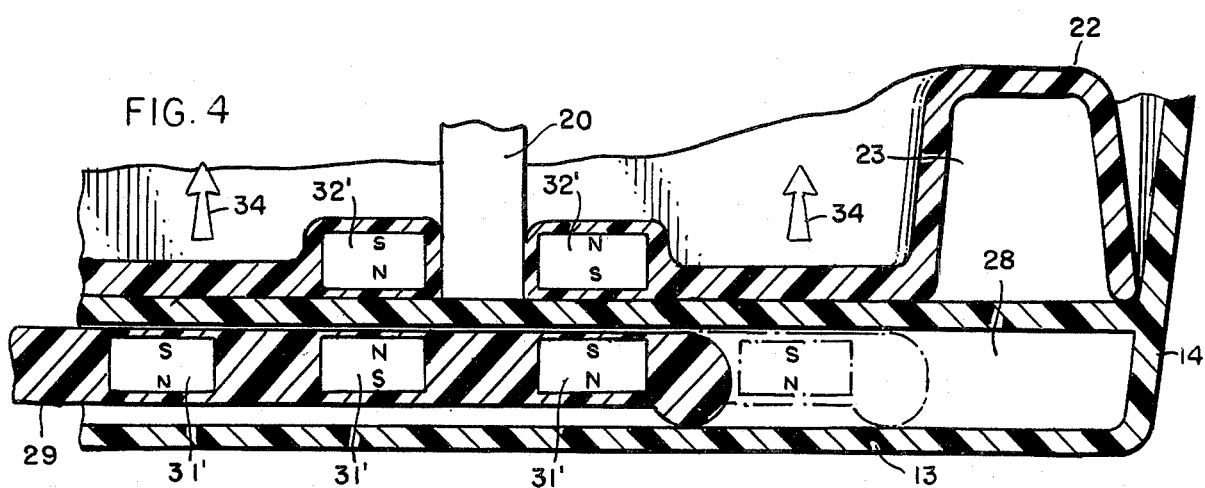
FIG. 4 is a fragmentary cross sectional view of a second embodiment of the invention.

The embodiment of FIG. 4 is the same as that of FIGS. 1-3 except for the magnetic means in slide member 29' and the bottom panel 21' of the tray. As somewhat schematically shown in the drawing, a pair of magnetic elements 32' are embedded within bottom panel 21, such magnetic elements taking the form of permanent magnets arranged with dissimilar poles facing downwardly. Slide member 29' carries three magnetic elements 31', only two of which are used when the slide member is in either its extended or inserted positions. The slide is shown in solid lines in its extended position, and it will be seen that the two magnetic elements 31' aligned with elements 32' are oriented so that the magnets of the respective sets attract each other. However, when the slide member is fully inserted (represented in broken lines), one of the magnetic elements 31' of the slide member (the magnetic element shown furthest to the right in FIG. 4) is shifted out of alignment, and the remaining two magnetic elements 31' of the slide member are repositioned with respect to elements 32' so that the sets of opposing magnetic elements have their poles arranged to repel each other. Therefore, with the slide member in the solid-line position of FIG. 4, the aligned magnetic elements 31' and 32' repel each other and urge the tray upwardly as indicated by arrows 34. While such repelling force drops off sharply as the buoyant tray moves away from bottom wall 13, such force is nevertheless of benefit in overcoming any friction or initial resistance to upward travel of the submerged tray.

While in the foregoing, I have disclosed embodiments of the invention in considerable detail for purposes of illustration, it will be understood by those skilled in the art that many of these details may be varied without departing from the spirit and scope of the invention.

I claim:

1. A tray and basin combination, said basin being formed of plastic material and having side and bottom walls defining an open-topped well for containing a treatment solution, said tray having a generally horizontal bottom panel for supporting articles to be treated and having horizontal dimensions corresponding with but slightly smaller than said well to permit said tray to be received for vertical movement between raised and lowered positions within said well, said side walls of said basin having a height substantially greater than said tray, lifting means for urging said tray into said raised position within said well, and magnetic anchoring means for retaining said tray in said lowered position within said well, said magnetic anchoring means including a slide member supported by said bottom wall for horizontal movement between first and second positions, and magnetic elements respectively secured to said slide member and said tray, said magnetic elements being oriented to attract each other and retain said tray in its lowered position against the force of said lifting means only when said slide member is in its first position, whereby, when said slide member is shifted from said first position to said second position, said tray is free to rise under the influence of said lifting means.

2. The combination of claim 1 in which said tray is formed of non-magnetic plastic material.

3. The combination of claim 2 in which said bottom panel of said tray is perforated.

4. The combination of claim 2 in which said tray has at least one handle joined to said tray for swinging movement between a vertical raised position and a generally horizontal lowered position.

5. The combination of claim 1 in which said lifting means comprises at least one air chamber formed in said tray.

6. The combination of claim 5 in which said air chamber extends about the periphery of said tray.

7. The combination of claim 6 in which said air chamber is formed by downwardly-extending parallel rims defining a downwardly-facing peripheral channel.

8. The combination of claim 5 in which said tray is formed of non-magnetic plastic material.

9. The combination of claim 1 in which said tray and basin are provided with guide means for guiding vertical movement of said tray between its raised and lowered positions.

10. The combination of claim 1 in which said bottom wall of said basin is provided with a horizontally-elongated compartment for slidably receiving said slide member, said slide member having a handle projecting outwardly from said basin for the manual shifting of said slide member between its first and second positions.

11. The combination of claim 10 in which said magnetic elements of said tray and slide member are disposed in vertical alignment for magnetic attraction to each other when said slide member is fully inserted into said compartment.

12. The combination of claim 11 in which the magnetic element of one of said tray and slide member is a permanent magnet and the magnet element of the other of said tray and slide member is formed of a ferromagnetic or paramagnetic material.

13. The combination of claim 12 in which the magnetic element of said slide member is a permanent magnet and the magnetic element of said tray is formed of ferromagnetic or paramagnetic material.

14. The combination of claim 11 in which the magnetic elements of both said tray and said slide member are permanet magnets arranged with opposite poles in facing relation when said slide member is in its first position and said tray is in its lowered position.

15. The combination of claim 14 in which said slide member is provided with a second magnetic element in the form of a permanent magnet alignable with the magnetic element of said tray when said slide member is in its second position, said second magnetic element of said slide member being oriented to repel the magnetic element of said tray when said slide member is in its second position.

* * * * *